US006277983B1

(12) United States Patent
Shaw et al.

(10) Patent No.: US 6,277,983 B1
(45) Date of Patent: Aug. 21, 2001

(54) REGIOSELECTIVE SYNTHESIS OF RAPAMYCIN DERIVATIVES

(75) Inventors: Chia-Cheng Shaw, Ville Saint Laurent; John Sellstedt, Lachine; Razzak Noureldin, Brossard; Gloria K. Cheal, LaSalle; Genevieve Fortier, Westmount, all of (CA)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/670,358

(22) Filed: Sep. 27, 2000

(51) Int. Cl.[7] .................................................. C07D 491/14
(52) U.S. Cl. ............................................................ 540/456
(58) Field of Search ............................. 540/456; 514/291

(56) References Cited

U.S. PATENT DOCUMENTS

| | | | |
|---|---|---|---|
| 4,316,885 | 2/1982 | Rakhit | 424/122 |
| 4,650,803 | 3/1987 | Stella et al. | 514/291 |
| 5,100,883 | 3/1992 | Schiehser | 514/183 |
| 5,118,677 | 6/1992 | Caufield | 514/183 |
| 5,118,678 | 6/1992 | Kao et al. | 514/183 |
| 5,120,842 | 6/1992 | Failli et al. | 540/452 |
| 5,130,307 | 7/1992 | Failli et al. | 514/321 |
| 5,151,413 | 9/1992 | Caufield et al. | 514/63 |
| 5,162,333 | 11/1992 | Failli et al. | 514/291 |
| 5,177,203 | 1/1993 | Failli et al. | 540/456 |
| 5,221,670 | 6/1993 | Caufield | 514/183 |
| 5,233,036 | 8/1993 | Hughes | 540/455 |
| 5,258,389 | 11/1993 | Goulet et al. | 514/291 |
| 5,260,300 | 11/1993 | Hu | 514/291 |
| 5,262,423 | 11/1993 | Kao | 514/291 |
| 5,302,584 | 4/1994 | Kao et al. | 514/80 |
| 5,362,718 | 11/1994 | Skotnicki et al. | 514/63 |
| 5,385,908 | 1/1995 | Nelson et al. | 514/291 |
| 5,385,909 | 1/1995 | Nelson et al. | 514/291 |
| 5,385,910 | 1/1995 | Ocain et al. | 514/291 |
| 5,387,680 | 2/1995 | Nelson | 540/456 |
| 5,389,639 | 2/1995 | Failli et al. | 514/291 |
| 5,391,730 | 2/1995 | Skotnicki et al. | 540/456 |
| 5,411,967 | 5/1995 | Kao et al. | 514/291 |
| 5,434,260 | 7/1995 | Skotnicki et al. | 514/291 |
| 5,463,048 | 10/1995 | Skotnicki et al. | 540/456 |
| 5,480,988 | 1/1996 | Failli et al. | 540/456 |
| 5,480,989 | 1/1996 | Kao et al. | 540/456 |
| 5,489,680 | 2/1996 | Failli et al. | 540/456 |
| 5,491,231 | 2/1996 | Nelson et al. | 540/456 |
| 5,504,091 | 4/1996 | Molnar-Kimber et al. | 514/291 |
| 5,563,145 | 10/1996 | Failli et al. | 514/291 |
| 5,665,772 | 9/1997 | Cottens et al. | 514/514 |
| 5,985,890 | 11/1999 | Cottens et al. | 514/291 |
| 6,015,809 | 1/2000 | Zhu et al. | 514/210 |

*Primary Examiner*—Bruck Kifle
(74) *Attorney, Agent, or Firm*—Arnold S. Milowsky

(57) ABSTRACT

This invention provides a regioselective process for preparing a 42-ester or ether of rapamycin, and 31-silyl ether intermediates.

13 Claims, No Drawings

REGIOSELECTIVE SYNTHESIS OF RAPAMYCIN DERIVATIVES

This application claims the benefit of U.S. Provisional Application No. Not Yet Known, which was converted from U.S. patent application Ser. No. 09/408,830, filed Sep. 29, 1999, pursuant to a petition filed under 37 C.F.R. 1.53(c)(2)(i).

BACKGROUND OF THE INVENTION

This invention relates to the regioselective synthesis of derivatives of rapamycin at the 42-position, which are useful for inducing immunosuppression, and in the treatment of transplantation rejection, graft vs. host disease, autoimmune diseases, diseases of inflammation, adult T-cell leukemia/lymphoma, solid tumors, fungal infections, and hyperproliferative vascular disorders.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31, 539 (1978); U.S. Pat. No. 3,929,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and U.S. Pat. No. 5,100,899].

Rapamycin has also been shown to be useful in preventing or treating systemic lupus erythematosus [U.S. Pat. No. 5,078,999], pulmonary inflammation [U.S. Pat. No. 5,080,899], insulin dependent diabetes mellitus [U.S. Pat. No. 5,321,009], smooth muscle cell proliferation and intimal thickening following vascular injury [U.S. Pat. No. 5,516,781], adult T-cell leukemia/lymphoma [European Patent Application 525,960 A1], and ocular inflammation [U.S. Pat. No. 5,387,589].

Numerous rapamycin 42-derivatives are known, typically being esters (carbon and sulfur based) or ethers of the 42-hydroxyl group of rapamycin, that are produced by esterification or etherification of the 42-position. Esterification of rapamycin at the 42-position was commonly prepared by directly reacting rapamycin with acylating agents in order to afford the desired product. The chemistry appeared to be rather simple. However, as rapamycin contains two secondary hydroxyl groups at positions 31 and 42, attempts to discriminate between these two functional centers in order to achieve a selective synthesis of 42-monoacylated product, posed a difficult challenge. This type of non-regioselective reaction also produced a 31,42-bis-acylated by-product and as well, some unreacted rapamycin remained in the reaction mixture. The final result was a lower yield that required extensive purification to obtain pure 42-monoacylated product.

DESCRIPTION OF THE INVENTION

This invention provides a regioselective method for the preparation of a 42-ester or ether rapamycin having the structure

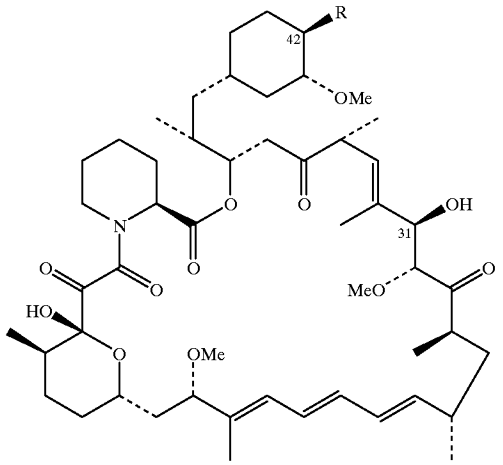

wherein R is an ester or ether, which comprises:

(a) treating rapamycin with a silylating agent to form rapamycin 31,42-bis-silyl ether;

(b) selectively hydrolyzing the 42-silyl ether in mild acid to provide rapamycin 31-silyl ether;

(c) treating the rapamycin 31-silyl ether with a suitable esterifying or etherifying reagent to form rapamycin 31-silyl ether 42-ester or ether; and (d) selectively hydrolyzing the 31-silyl ether in mild acid to provide the desired rapamycin 42-ester or ether.

Preferred 42-esters and ethers of rapamycin which can be prepared by the method provided by this invention are disclosed in the following patents, which are all hereby incorporated by reference: alkyl esters (U.S. Pat. No. 4,316,885); aminoalkyl esters (U.S. Pat. No. 4,650,803); fluorinated esters (U.S. Pat. No. 5,100,883); amide esters (U.S. Pat. No. 5,118,677); carbamate esters (U.S. Pat. No. 5,118,678); silyl ethers (U.S. Pat. No. 5,120,842); aminoesters (U.S. Pat. No. 5,130,307); acetals (U.S. Pat. No. 5,51,413); aminodiesters (U.S. Pat. No. 5,162,333); sulfonate and sulfate esters (U.S. Pat. No. 5,177,203); esters (U.S. Pat. No. 5,221,670); alkoxycsters (U.S. Pat. No. 5,233,036); O-aryl, -alkyl, -alkenyl, and -alkynyl ethers (U.S. Pat. No. 5,258,389); carbonate esters (U.S. Pat. No. 5,260,300); arylcarbonyl and alkoxycarbonyl carbamates (U.S. Pat. No. 5,262,423); carbamates (U.S. Pat. No. 5,302,584); hydroxyesters (U.S. Pat. No. 5,362,718); hindered esters (U.S. Pat. No. 5,385,908); heterocyclic esters (U.S. Pat. No. 5,385,909); gem-disubstituted esters (U.S. Pat. No. 5,385,910); amino alkanoic esters (U.S. Pat. No. 5,389,639); phosphorylcarbamate esters (U.S. Pat. No. 5,391,730); carbamate esters (U.S. Pat. No. 5,411,967); carbamate esters (U.S. Pat. No. 5,434,260); amidino carbamate esters (U.S. Pat. No. 5,463,048); carbamate esters (U.S. Pat. No. 5,480,988); carbamate esters (U.S. Pat. No. 5,480,989); carbamate esters (U.S. Pat. No. 5,489,680); hindered N-oxide esters (U.S. Pat. No. 5,491,231); biotin esters (U.S. Pat. No. 5,504,091); and O-alkyl ethers (U.S. Pat. No. 5,665,772). These patents also disclose methods for esterification or etherification utilized in step (c), above.

The following scheme illustrates the regioselective preparation of rapamycin 42-ester with 2,2-bis-(hydroxymethyl) propionic acid, as a representative 42-ester of rapamycin, which can be prepared according to the method provided in this invention. The original synthesis of rapamycin 42-ester with 2,2-bis-(hydroxymethyl)propionic acid is disclosed in U.S. Pat. No. 5,362,718.

Scheme I
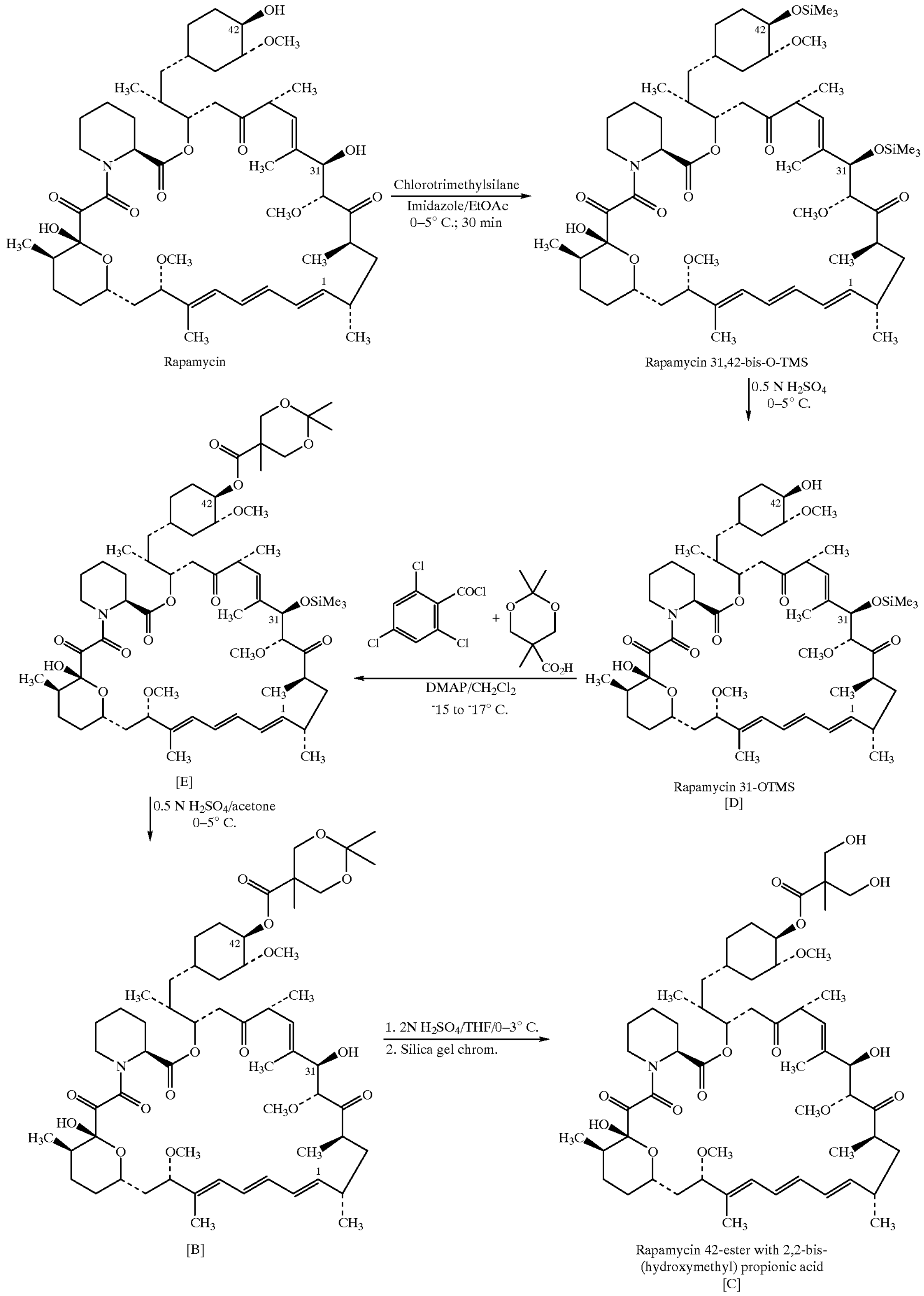
Rapamycin
Rapamycin 31,42-bis-O-TMS
Rapamycin 31-OTMS
[D]
[E]
[B]
Rapamycin 42-ester with 2,2-bis-(hydroxymethyl) propionic acid
[C]

While the chemical preparation of rapamycin esters and ethers appears to be simple, and the desired products are obtainable, the synthetic yield of the esters and ethers is often poor. As rapamycin contains two secondary hydroxyl groups at positions 31 and 42, attempts to discriminate between these two functional centers in order to achieve a selective synthesis of 42-monoester such as compound [B] poses a difficult challenge. For example, the synthesis of rapamycin 42-ester with 2,2-bis-(hydroxymethyl)propionic acid described in U.S. Pat. No. 5,362,718, example 10, was non-regioselective, the 31,42-bisester by-product was also generated. As a result, the crude product [B] after work-up contains the desired product [B], 31,42-bisester by-product and unreacted rapamycin. In an effort to consume the remaining starting rapamycin, the reaction was allowed to proceed for a longer period with negative consequences, the quantity of the 31,42-bisester increased significantly. The resulting crude product [B] is contaminated with unreacted rapamycin and 31,42-bisester, and subsequent column chromatography purification effort has proved to be difficult as the 42,31-bisester has a very close retention time with product [B]. Overall, the major obstacle in large-scale production of compound [B] appears to be the non-regiospecificity that is further complicated by purification difficulties. This invention overcomes these difficulties by providing a regioselective synthesis of 42-esters or ethers of rapamycin by selectively protecting the 31-hydroxyl group as a silyl ether (i.e., compound [D]), leaving the 42-position hydroxyl accessible for regioselective esterification or etherification to produce 31-O-silyl, 42-esters or ethers (i.e., compound [E]). The 31-hydroxyl group can then be deprotected under mild acidic conditions (i.e., compound [B]).

In accordance with this invention, it is preferred that the 31, and 42-hydroxyl groups are protected as trialkyl silyl ethers. The 42-silyl protected hydroxyl group of the 31, 42-bis-silylated rapamycin can be selectively cleaved under mildly acidic conditions to provide 31-silyl rapamycin. The silylating agents used for this transformation are common, commercially available chloroalkylsilanes, such as chlorotrimethylsilane, chlorotrimethylsilane or chlorotripropylsilane. However, the bulkier the trialkylsilane, the more time is needed to deprotect in acid media during the penultimate chemical step to regenerate the 31-hydroxyl group. Also, a longer reaction time in the acid media generates more degradation by-products. Although, chlorotrimethylsilane, chlorotrimethylsilane or chlorotripropylsilane can be used for the preparation of rapamycin 31-O-trialkylsilyl ethers, chlorotrimethylsilane is the preferred silylating agent. The trimethylsilyl group is more acid labile and therefore easier to de-protect during the transformation and in effect, this minimizes the formation of degradation products. The preparation of 31-O-trimethylsilyl rapamycin [D] is described in Example 1. Rapamycin is treated with excess chlorotrimethylsilane in ethyl acetate at 0–5° C. in the presence of an organic base and the 42- and 31-hydroxyl groups of rapamycin are silylated to form rapamycin 31, 42-bis-O-trimethylsilyl ether in quantitative yield. The common organic bases such as imidazole, 1-methylimidazole, triethylamine and N, N-diisopropylethylamine can be used for the general silylation reaction. However, imidazole is found to be the preferred base for the silylation of rapamycin as the reaction is completed within 30 minutes.

Selective de-protection of the 42-O-trimethylsilyl group of rapamycin 31,42-bis-O-trimethylsilyl ether to form rapamycin 31-O-trimethylsilyl ether, is effected in situ at 0–5° C. with ethanol, ethanol-water mixtures, water, diluted inorganic or organic acids. Sulfuric acid (0.5 N) is preferred since the reaction is clean and can be completed in 4–5 h. A number of organic solvents can be used for silylation and in particular, DMF is often mentioned in the literature. However, in this invention, ethyl acetate is the preferred solvent.

The esterification or etherification of the 31-protected rapamycin can be carried out under conditions described in the patents listed above. For example, in Scheme I, the acylation of rapamycin 31-trimethylsilyl ether was accomplished using 2,4,6-trichlorobenzyl mixed anhydride of 2,2,5-trimethyl[1.3-dioxane]-5-carboxylic acid in the presence of 4-dimethylaminopyridine or a similar reagent. In addition, 2,2,5-trimethyl[1.3-dioxane]-5-carboxylic acid chloride was also found to be an effective acylation agent in this invention in the presence of 4-dimethylaminopyridine or a similar reagent. For the acylation conditions, methylene chloride is the preferred solvent rather than tetrahydrofuran which was described in the prior art. In addition, lower reaction temperature of less than 0° C., with −20 to −15° C. or lower being more preferred, provides better results than the room temperature acylation described in U.S. Pat. No. 5,362,718. In Scheme I, the acylation products, 31-O-TMS, 42-(protected-hydroxy) esters (compound [E]) can be further treated with diluted acid to convert them to 42-(protected-hydroxy) esters (compound [B]) or used directly to make final product 42-hydroxyesters (final product [C]). This methodology can be used to prepare other esters or ethers of rapamycin, by simply varying the esterifying or etherifying agent used.

In Scheme I, conversion of compound [B] to rapamycin 42-ester with 2,2-bis-(hydroxymethyl)propionic acid [C], can be accomplished under mildly acidic conditions. It is preferred that aqueous sulfuric acid is used, as it minimizes the formation of impurities generated when aqueous hydrochloric acid is used, as described in the U.S. Pat. No. 5,362,718. The tetraene impurity formed when using hydrochloric acid has been reported to be difficult to separate from the desired product by column chromatography (Caufield et al, Tetrahedron Lett., 1994, 37,6835). It is also preferable to carry out the hydrolysis at 0–5° C. rather than room temperature as described in U.S. Pat. No. 5,362,718.

The synthetic route disclosed in this invention provides several distinct advantages over the synthetic methodology which has been published for the preparation of rapamycin esters or ethers; mainly in the yield and ease of purification of the desired 42-esters or ethers. As this is a regioselective synthesis, the overall yields of the desired 42-esters or ethers is dramatically improved. For example, the synthetic methodology taught in U.S. Pat. No. 5,362,718 provides compound [B] in a 35% yield, whereas, the synthesis of [B] is accomplished in 85% yield using the methodology disclosed herein. Additionally, the conversion to rapamycin 42-ester with 2,2-bis-(hydroxymethyl)propionic acid from [B] is accomplished in approximately 75% yield using the process described herein, whereas only a 20% conversion is provided using the methodology of U.S. Pat. No. 5,362,718.

Using the same methodology, 42-ethers of rapamycin can be prepared in a regioselective manner. As an example, U.S. Pat. No. 5,665,772 discloses the preparation of 40-O-alkyl ethers of rapamycin in a non-regioselective manner. Owing to nomenclature differences, the 42-position of rapamycin (as named in this invention) is referred to as the 40-position in U.S. Pat. No. 5,665,772. These positions are identical. Using the methodology disclosed herein, rapamycin 31-O-trimethylsilyl ether can be treated with, for example, 2-(t-butyldimethylsilyl)oxyethyl triflate) to provide 31-O- trimethylsilyl, 42-O-[2-(t-butyldimethylsilyl)oxy]ethyl-rapamycin. Removal of the silyl protecting groups from the 31-hydroxyl group of rapamycin and from the 42-hydroxyethyl moiety can be accomplished under mildly acidic conditions, such as dilute sulfuric acid to provide 42-O-(2-hydroxy)ethyl rapamycin. The non-regioselective formation of other 42-ethers of rapamycin is disclosed in U.S. Pat. No. 5,665,772. These also can be prepared regioselectively via rapamycin 31-O-trimethylsilyl ether.

This invention also covers 31-silyl ethers of rapamycin, which arc useful in the preparation of the 42-esters and ethers of rapamycin, as disclosed herein. The silicon moiety as represented by —SiR'R"R"', contains 3 groups which can be the same or different. Typical silyl ethers of this invention contain R', R", or R"' moieties which are alkyl of 1–6 carbon atoms, phenyl, or benzyl groups. The alkyl groups can be branched or straight chain. It is preferred that R', R", and R"' be alkyl groups, and more preferred that R', R", and R"' are methyl or ethyl. It is still more preferred that the 31-silyl ether is rapamycin 31-O-trimethylsilyl ether.

The following examples illustrate the preparation of rapamycin 31-silyl ethers and a rapamycin 42-ester, which is representative of the compound which can be prepared by the process of this invention.

EXAMPLE 1

Rapamycin 31-O-trimethylsilyl ether

A solution of rapamycin (25.0 g, 92.4% strength; 25.28 mmol) in 750 mL ethyl acetate was cooled to 0–5° C.; 7.5 g (110.20 mmol) of imidazole was added and stirred to form a solution. To this cold solution 11.0 g (101.25 mmol) of chlorotrimethylsilane was added dropwise over 30 min and stirred for a further 30 min at 0–5° C. in order to complete the formation of rapamycin 31,42-bis-O-trimethylsilyl ether. A 50 mL quantity of 0.5 N sulfuric acid was added dropwise over a 10 min period and the mixture was stirred for 2.5 h at 0–5° C. The reaction mixture was transferred into a separatory funnel and the aqueous layer was separated and extracted with 125 mL ethyl acetate. The organic layers were combined and successively washed with brine (125 mL), saturated sodium bicarbonate solution (100 mL), water (125 mL×2) then brine to pH 6–7. The organic layer was dried over anhydrous sodium sulfate and evaporated under reduced pressure to give a beige color foam product, 28.5 g (theory 24.94 g). HPLC analysis showed it contained 86% (by area %) of rapamycin 31-O-trimethylsilyl ether and 7% of rapamycin. The product was used directly for the subsequent reaction.

LC/MS electrospray (+) mode (M−H)=985. $^1$H NMR (400 MHz, d-6 DMSO) δ 4.60 (m, 1H, (42C)OH), 4.10 (m, 1H, C(31) H), 3.09 (m, 1H, C(42) H), −0.027 (s, 9H, 31-O-TMS).

EXAMPLE 2

2,2,5-Trimethyl[1.3-dioxane]-5-carboxylic acid chloride

A solution of 2,2,5-trimethyl[1.3-dioxane]-5-carboxylic acid (17.42 g, 0.1 mol) in 200 mL of dry toluene was warmed to 40° C., and 26.0 mL of oxalyl chloride (37.83 g, 0.3 mol) added dropwise over a period of 30 min and then stirred at 40° C. for 2.5 h. The reaction mixture was evaporated under reduced pressure to remove solvent and excess oxalyl chloride. The residual product was evaporated twice with dry toluene (200 mL), then dried under high vacuum at 40° C. for 2 h to obtain 19.75 g of product as an orange colored liquid. $^1$H NMR (300 MHz, $CDCl_3$) 6 4.28 (2H, d, J=10.5 Hz), 3.76 (2H, d, J=10.5 Hz),1.46 (3H, s), 1.29 (3H, s). $^{13}$C NMR (75 MHz, $CDCl_3$) δ 176.43, 98.76, 66.06, 52.07, 25.82, 21.20, 18.10.

EXAMPLE 3

Rapamycin 31-O-trimethylsilyl ether, 42-ester with 2,2,5-trimethylyl[1.3-dioxane]-5-carboxylic acid Method A:

To a solution of the 2,2,5-trimethyl[1.3-dioxane]-5-carboxylic acid (9.77 g, 56.08 mmol) and N,N-diisopropylethylamine (12.00 g, 92.80 mmol) in 200 mL methylene chloride at room temperature under nitrogen, 2,4,6-trichlorobenzyl chloride (13.35 g, 54.73 mmol) was added and the resulting mixture was stirred for 5 h at room temperature. The reaction mixture was cooled to −20 to −15° C. and a solution of rapamycin 31-O-trimethylsilyl ether (28.50 g, crude, made from 25.28 mmol of rapamycin) in 120 mL methylene chloride was added. A solution of 4-dimethylaminopyridine (11.68 g, 95.60 mmol) in 110 mL methylene chloride was added dropwise over a 2 h period. The reaction mixture was further stirred for 16 h at −15 to −16° C. The reaction mixture was quenched with 100 mL water and the organic layer was separated and washed with 0.5 N sulfuric acid (180 mL), followed by brine (100 mL), saturated sodium bicarbonate solution (100 mL), water (100 mL×2), brine (100 mL) to pH 6–7. The organic layer was dried over anhydrous sodium sulfate and evaporated under reduced pressure to afford the title compound (33.18 g) as a beige color foam.

LC/MS electrospray (+) mode (M+$NH_4$)=1160. $^1$H NMR (400 MHz, d-6 DMSO) δ 4.57 (m, 1H, C(42)H), 4.10 (m, 1H, C(31) H), 4.03 (d, 2H), 3.57 (d, 2H), 1.34 (s, 3H), 1.24 (s, 3H), 1.13 (s, 3H), -0.023 (s, 9H, 31-O-TMS)

Method B:

A solution of rapamycin 31-O-trimethylsilyl ether (11.00 g; from 10.0 g of rapamycin; 11.15 mmol) in 120 mL methylene chloride, containing 2 mL of N,N,-dimethylformamide, was stirred under nitrogen and cooled to −15° C., 4-dimethylaminopyridine (4.80 g, 39.29 mmol) was added and the mixture was stirred to form a solution. To this cold solution a 7.5% solution of 2,2,5-trimethyl[1.3-dioxane]-5-carboxylic acid chloride (42.18 g; 16.42 mmol) in methylene chloride was added dropwise over a 2 h period. The solution was further stirred for 1 h at −15° C., and an additional 7.5% solution of acid chloride (14.06 g, 5.47 mmol) in methylene chloride was added over a 30 min period. The reaction mixture was further stirred for 16 h at −15° C. to −16° C. The reaction mixture was quenched with 100 mL brine and the organic layer was separated and washed with cold 0.5 N sulfuric acid (100 mL), brine (100 mL), saturated sodium bicarbonate solution (100 mL) water (100 mL), brine (100 mL) to pH 6–7. The organic layer was dried over anhydrous sodium sulfate and evaporated under reduced pressure to afford product (12.15 g) as a yellow foam.

EXAMPLE 4

Rapamycin 42-ester with 2,2,5-trimethyl[1.3-dioxane]-5-carboxylic acid

A solution of rapamycin 31-O-trimethylsilyl ether, 42-ester with 2,2,5-trimethyl[1.3-dioxane]-5-carboxylic acid (33.18 g; from example 3, method A) in 100 mL of acetone was stirred and cooled to 0–5° C. To this cold solution 17 mL of 0.5 N sulfuric acid was added dropwise over a 10 min period and the mixture was stirred for 2.5 h at 0–5° C. A solution of sodium bicarbonate (1.44 g) in 20 mL water was added over a period of 20 min followed by an additional 33 mL water over a period of 30 min; the product started to precipitated after about 1 h of stirring. The mixture was stirred overnight at 0–5° C. and after filtration the solid product was washed with 60 mL of acetone-water (1:1). The product was dried in a vacuum oven at 30° C. to obtain 28.85 g of product (83.9% strength, 89.3% overall yield from rapamycin). The $^1$H NMR of the product was identical to the product described in U.S. Pat. No. 5,362,718 example 10.

EXAMPLE 5

Rapamycin 42-ester with 2,2-bis-(hydroxymethyl) propionic acid

Method A:

A solution of rapamycin 42-ester with 2,2,5-trimethyl [1.3-dioxane]-5-carboxylic acid (28.85 g; from example 4) in 276 mL of tetrahydrofuran was stirred and cooled to 0–5° C. To this cold solution 83 mL of cold 2 N sulfuric acid was added dropwise over a 30 min period and the mixture was stirred for 60 h at 0–5° C. The reaction mixture was diluted with 600 mL of ethyl acetate and washed with 120 mL brine. The aqueous layer was extracted once with 120 mL of ethyl acetate and the organic extracts were combined and washed with saturated sodium bicarbonate solution (120 mL), water (200 mL×2) and brine (120 mL) to pH 6–7. The organic phase was dried over anhydrous sodium sulfate and evaporated under reduced pressure at room temperature to obtain product (28.42 g), as a beige color foam. The crude product was chromatographed on a silica gel column and eluted with 30% acetone in heptane to give 18.06 g of pure product, a white solid (69.4% overall from rapamycin). The $^1$H NMR of the product is identical to the product described in U.S. Pat. No. 5,362,718 example 11.

Method B:

A solution of rapamycin 31-O-trimethylsilyl ether, 42-ester with 2,2,5-trimethyl[1.3-dioxane]-5-carboxylic acid (23.25 g, prepared from 20.06 g of rapamycin, strength 92.7%, 20.34 mmol) in 230 nL of tetrahydrofuran was stirred and cooled to 0–5° C. To this cold solution 115 mL of cold 2 N sulfuric acid was added dropwise over a 45 min period and the mixture was stirred for 88 h at 0–5° C. The reaction mixture was diluted with 500 mL of ethyl acetate and washed with 100 mL brine. The aqueous layer was extracted once with 100 mL of ethyl acetate and the organic extracts were combined and washed with saturated sodium bicarbonate solution (80 mL), water (80 mL×2) and brine (100 mL) to pH 6–7. The organic phase was dried over anhydrous sodium sulfate and evaporated under reduced pressure at room temperature to afford product (22.48 g), a beige color foam. The crude product was chromatographed on a silica gel column and eluted with 30% acetone in heptane to give 16.50 g of pure product as a white solid (78.4% overall from rapamycin). The $^1$H NMR of the product is identical to the product described in U.S. Pat. No. 5,362,718 example 11.

EXAMPLE 6

Rapamycin 31,42-bis-O-trimethylsilyl ether

A solution of rapamycin (10.0 g, 94.3% strength; 10.3 mmol) in 150 mL ethyl acetate was cooled to 0–5° C.; 3.0 g (44 mmol) of imidazole was added and stirred to form a solution. To this cold solution, 4.4 g (40.5 mmol) of chlorotrimethylsilane was added dropwise over a 20 min period and following this, the solution was stirred at 0–5° C. for a further 30 min. The reaction mixture was filtered to remove the imidazole HCl and the filtrate was evaporated under reduced pressure to obtain a yellow foam. Heptane (200 mL) was added and stirred at room temperature for 20 min and the mixture was filtered. The filtrate was washed with 40 mL of saturated sodium bicarbonate solution, then twice with water (80 mL), then brine (50 mL). The organic layer was dried over anhydrous sodium sulfate and evaporated to obtain the product, a yellow foam of 11.42 g (98.6%).

LC/MS electrospray (–) mode (M–H)=1057. $^1$H NMR (400 MHz, d-6 DMSO) δ 4.10 (m, 1H, C(31) H), 3.31 (m, 1H, C(42) H), 0.057 (s, 9H, 42-O-TMS), -0.027 (s, 9H,31-O-TMS).

EXAMPLE 7

Rapamycin 31-O-triethylsilyl ether

A solution of rapamycin (5.00 g, 92.7% strength; 5.07 mmol) in 75 mL ethyl acetate was cooled to 0–5° C.; 1.50 g (22.03 mmol) of imidazole was added and stirred to form a solution. To this cold solution, 3.05 g (20.23 mmol) of chlorotrimethylsilane was added dropwise over a 10 minutes period. The mixture was stirred for 30 min at 0–5° C., then stirred at room temperature overnight to complete the formation of rapamycin 31,42-bis-O-triethylsilyl ether. Following filtration of the reaction mixture, the filtrate was evaporated under reduced pressure at room temperature to remove most of the solvent. The residual solution (ca. 10 mL) was dissolved in 60 mL acetone and 15 mL of 0.15 N sulfuric acid was added and the mixture stirred for 25 h at 0–5° C. The rapamycin 31,42-bis-O-triethylsilyl ether disappeared at this stage. The reaction mixture was diluted with 80 mL of ethyl acetate and successively washed with brine (60 mL×2), saturated sodium bicarbonate solution (40 mL), water (60 mL×2), brine (60 mL) to pH 6–7. The organic layer was dried over anhydrous sodium sulfate and evaporated under reduced pressure to obtain a product of light yellow gum, 6.92 g (theory 5.21 g). HPLC analysis showed it contained 95.2% (by area %) rapamycin 31-O-triethylsilyl ether and 0.9% rapamycin.

EXAMPLE 8

Rapamycin 31-O-tripropylsilyl ether

A solution of rapamycin (5.00 g, 92.7% strength; 5.07 mmol) in 75 mL ethyl acetate was cooled to 0–5° C.; 1.50 g (22.03 mmol) of imidazole was added and stirred to form a solution. To this cold solution, 3.91 g (20.3 mmol) of chlorotripropylsilane was added dropwise over 10 min period. The mixture was stirred for 30 min at 0–5° C., then at room temperature for 21 h to complete the formation of rapamycin 31,42-bis-O-tripropylsilyl ether. Following filtration of the reaction mixture, the filtrate was evaporated under reduced pressure at room temperature to remove most of the solvent and the residual solution was dissolved in 60 mL acetone. A 15 mL quantity of 0.25 N of sulfuric acid was added and the mixture was stirred for 45 h at 0–5° C.; the rapamycin 31,42-bis-O-tripropylsilyl ether disappeared at this stage. The reaction mixture was diluted with 100 mL of ethyl acetate, and successively washed with brine (40 mL×2), saturated sodium bicarbonate solution (40 mL), water (40 mL×2), and brine (50 mL) to pH 6–7. The organic layer was dried over anhydrous sodium sulfate and evaporated under reduced pressure to obtain a product of light yellow gum, 8.07 g (theory 5.43 g). HPLC analysis showed it contained 96.7% (by area %) of rapamycin 31-O-tripropylsilyl ether and 1% of rapamycin.

What is claimed is:

1. A process for preparing rapamycin 31-trimethylsilyl ether, which comprises:

(a) treating rapamycin with chlorotrimethylsilane in an inert solvent in the presence of a suitable base to provide rapamycin 31,42-bis-trimethylsilyl ether; and (b) treating the 31,42-bis-trimethylsilyl ether with dilute acid to provide rapamycin 31-trimethylsilyl ether.

2. The process according to claim 1, wherein the base in step (a) is imidazole, 1-methylimidazole, triethylamine, or N,N-diisopropylethylamine.

3. The process according to claim 2, wherein the acid in step (b) is sulfuric acid.

4. A process for preparing rapamycin 42-ester with 2,2-bis-(hydroxymethyl)propionic acid, which comprises:

(a) treating rapamycin with a silylating agent to form rapamycin 31,42-bis-silyl ether;

(b) selectively hydrolyzing the 42-silyl ether in mild acid to provide rapamycin 31-silyl ether;

(c) acylating the rapamycin 31-silyl ether with 2,2,5-trimethyl[1.3-dioxane]-5-carboxylic acid chloride or the 2,4,6-trichlorobenzyl mixed anhydride of 2,2,5-trimethyl[1.3-dioxane]-5-carboxylic acid to give rapamycin 31-O-trimethylsilyl ether, 42-ester with 2,2,5-trimethyl[1.3-dioxane]-5-carboxylic acid;

(d) selectively hydrolyzing the 31-silyl ether in mild dilute acid to provide rapamycin 42-ester with 2,2,5-trimethyl[1.3-dioxane]-5-carboxylic acid; and (e) treatment of rapamycin 42-ester with 2,2,5-trimethyl [1.3-dioxane]-5-carboxylic acid with mild acid to provide 42-ester with 2,2-bis-(hydroxymethyl)propionic acid.

5. The process according to claim 4, wherein the silylating agent is a trialkylsilyl halide.

6. The process according to claim 5, wherein the silylating agent is chlorotrimethylsilane.

7. The process according to claim 6, wherein the acid used in steps (b) and (d) is sulfuric acid.

8. The process according to claim 7, wherein the acylation in step (c) is carried out at less than 0° C.

9. A process for preparing 42-O-(2-hydroxy)ethyl-rapamycin which comprises:

(a) treating rapamycin with a silylating agent to form rapamycin 31,42-bis-silyl ether;

(b) selectively hydrolyzing the 42-silyl ether in mild acid to provide rapamycin 31-silyl ether;

(c) treating the rapamycin 31-silyl ether with a an ethylene glycol equivalent containing an acid labile hydroxyl protecting group protecting on one terminus of the ethylene glycol equivalent and a leaving group suitable of alkylating a hydroxyl group as the other terminus of the ethylene glycol equivalent (d) hydrolyzing the protecting groups on the 31-position and on the 42-hydroxyethyl position under mildly acidic conditions.

10. The process according to claim 9, wherein the silylating agent is trialkylsilyl halide.

11. The process according to claim 10, wherein the silylating agent is chlorotrimethylsilane.

12. The process according to claim 11, wherein the ethylene glycol equivalent is 2-(t-butyldimethylsilyl) oxyethyl triflate).

13. The process according to claim 12, wherein the acid used in steps (b) and (d) is sulfuric acid.

* * * * *